United States Patent
Ledoussal et al.

(10) Patent No.: US 6,509,349 B1
(45) Date of Patent: Jan. 21, 2003

(54) ANTIMICROBIAL 2-PYRIDONES, THEIR COMPOSITIONS AND USES

(75) Inventors: Benoit Ledoussal, Mason, OH (US); Sean M. Flaim, Toledo, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/020,709

(22) Filed: Dec. 14, 2001

Related U.S. Application Data

(60) Provisional application No. 60/255,628, filed on Dec. 14, 2000.

(51) Int. Cl.$^7$ ................... A61K 31/435; C07D 471/04

(52) U.S. Cl. ...................... 514/306; 546/138

(58) Field of Search ........................ 546/138; 514/306

(56) References Cited

U.S. PATENT DOCUMENTS

| | | | |
|---|---|---|---|
| 4,844,902 A | | 7/1989 | Grohe |
| 5,072,001 A | | 12/1991 | Hagen et al. |
| 5,229,396 A | | 7/1993 | Brighty |
| 5,328,908 A | | 7/1994 | Demuth, Jr. et al. |
| 5,412,098 A | | 5/1995 | Yasuhiro et al. |
| 5,457,104 A | | 10/1995 | Bartel et al. |
| 5,556,979 A | | 9/1996 | Phillips et al. |
| 5,580,872 A | * | 12/1996 | Chu et al. ............ 514/254 |
| 5,599,816 A | | 2/1997 | Chu et al. |
| 5,726,182 A | | 3/1998 | Chu et al. |

FOREIGN PATENT DOCUMENTS

| | | |
|---|---|---|
| EP | 0308019 A2 | 3/1989 |
| EP | 0413455 B2 | 7/1990 |
| EP | 0572259 A1 | 1/1993 |
| EP | 0775702 A1 | 5/1997 |
| EP | 0947513 A1 | 10/1997 |
| FR | 2656-611 A1 | 7/1991 |
| JP | 62-255482 | 11/1987 |
| JP | 03-115277 | 5/1991 |
| JP | 09-136886 | 5/1997 |
| JP | 09002953 | 7/1997 |
| JP | 10287669 | 10/1998 |
| WO | WO 91/16894 A1 | 11/1991 |
| WO | WO 95/10519 A1 | 4/1995 |
| WO | WO 98/52939 A1 | 5/1997 |
| WO | WO 98/54169 A | 5/1997 |
| WO | WO 99/07696 A1 | 2/1999 |

OTHER PUBLICATIONS

Li et al., J. Med. Chem., (1996) vol. 39, pp. 3070–3088.*
Albrecht, "Develolpment of Antibacterial Agents of the Nalidixic Acid Type", *Prog. In Drug Research*, 1977, pp. 9–104, vol. 21.
Wolfson et al., "The Fluoroquinolones: Structures, Mechanisms of Action and Resistance, and Spectra of Activity In Vitro", *Antimicrobial Agents and Chemotherapy*, 1985, pp. 581–586, vol. 28, No. 4.

Klopman et al., "Computer Automated Structure Evaluation of Quinolone Antibacterial Agents", *Antimicrobial Agents and Chemotherapy*, 1987, pp. 1831–1840, vol. 31, No. 11.

Wentland et al., "Quinolone Antibacterial Agents", *Annual Reports in Medicinal Chemistry*, 1986, pp. 145–154, Vol. 20, Chapter 15.

Cornett et al., "Quinolone Antibacterial Agents", *Annual Reports in Medicinal Chemistry*, 1986, pp. 139–148, vol. 21, Chapter 14.

White et al., "Quinolones", *Annual Reports in Medicinal Chemistry*, 1987, pp. 117–126, vol. 22, Chapter 12, Section III—Chemotherapeutic Agents.

Koga et al., "Structure–Activity Relationships of Antibacterial 6,7–and 7,8–Disubstituted 1–alkyl–1,4–dihydro—4–oxoquinoline–3–carboxylic Acids.", *J. Med. Chem.*, 1980, pp. 1358–1363, vol. 23.

Domagala et al., "1–Substituted 7–[3–(Ethylamino)-methyl]–1–pyrrolidinyl–6, 8–difuoro–4–oxo–3–quinoline-carboxylic Acids. New Quantitative Structure–Activity Relationships at $N_1$ for the Quinolone Antibacterials", *J. Med. Chem.*, 1988, pp. 991–1001, vol. 31.

Rosen et al., "Asymmetric Synthesis and Properties of the Enantiomers of the Atibacterial Agent 7–(3–Amino-pyrrolidin–1–yl)–1–(2,4–difluorophenyl)–1,4–dihydro–6–fluoro–4–oxo–1,8–naphthyridine–3–carboxylic Acid Hydrochloride", *J. Med. Chem.*, 1988, pp. 1586–1590, vol. 31.

Rosen et al., "Design, Synthesis, and Properties of (4S)–7–(4–Amio–2–substituted–pyrrolidin–1–yl) quinolone–3–carboxylic Acids", *J. Med. Chem.*, 1988, pp. 1598–161, vol. 31.

Ledoussal et al., "Potent Non–6–Fluoro Substituted Quinolone Antibacterials: Synthesis and Biological Activity", *J. Med. Chem.*, 1992, pp. 198–200, vol. 35.

(List continued on next page.)

*Primary Examiner*—Bernard Dentz
(74) *Attorney, Agent, or Firm*—David V. Upite; Carl J. Roof

(57) ABSTRACT

Compounds having the general structure:

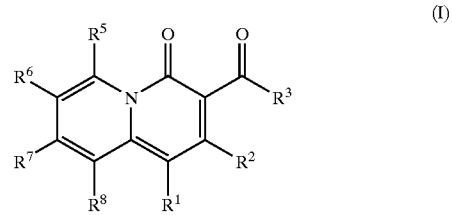

are effective antimicrobial agents.

17 Claims, No Drawings

OTHER PUBLICATIONS

Donogala et al., "Quinolone Antibacterial Containing the New 7-[3-(1-Aminoethyl)-1-pyrrolidinyl]Side Chain: The Effects of the 1-Aminoethyl Moiety and Its Stereochemical Configurations on Potency and in Vivo Efficacy", *J. Med. Chem.*, 1993, pp. 871–882, vol. 36, No. 7.

Hagen et al., "Synthesis and Antibacterial Activity of New Quinolones Containing a 7-[3-(1-Amino-1-methylethyl)-1-pyrrolidinyl] Moiety. Gram–Positive Agents with Excellent Oral Activity and Low Side–Effect Potential", *J. Med. Chem.*., 1994, pp. 733–738, vol. 37, No. 6.

Cecchetti et al., "Studies on 6–Aminoquinolones: Synthesis and Antibacterial Evaluation of 6–Amino–8–methylquinolones", *J. Med. Chem.*, 1996, pp. 436–445, vol. 39, No. 2.

Cecchetti et al., "Potent 6–Desfluoro–8–methylquinolones as New Lead Compounds in antibacterial Chemotheerapy", *J. Med. Chem.*, 1996, pp. 4952–4957, vol. 39, No. 25.

Hong et al., "Novel 5–Amino–6–Methylquinolone Antibacterials: A New Class of Non–6–Fluoroquinolones", *Bioorganic & Medicinal Chem Letts.*, 1997, pp. 1875–1878, vol. 7, No. 14.

Gun et al., "Synthesis and Stucture—Activity Relationships of 2–Pyridones: A Novel Series of Potent DNA Gyrase Inhibitors as Antibacterial Agents", *J. Med. Chem.*, 1996, pp. 3070–3088, vol. 39.

Sanders et al., "Inducible β–Lactamases: Clinical and Epidemiologic Implications for Use of Newer Cephalosporins", *Reviews of Infectious Deiseases*, Jul.–Aug. 1988, pp. 830–838, vol. 10, No. 4.

Ma et al, "Synthesis and Antimicrobial Activity of 4H–4–Oxoquinolizine Derivatives: Consequences of Structural Modification at the C–8 Position", *J. Med. Chem.*, 1999, pp. 4202–4213,. vol. 42, No. 20.

* cited by examiner

ANTIMICROBIAL 2-PYRIDONES, THEIR COMPOSITIONS AND USES

CROSS REFERENCE

This application claims priority under Title 35, United States Code 119(e) from Provisional Application Serial No. 60/255,628, filed Dec. 14, 2000.

FIELD OF THE INVENTION

The subject invention relates to novel antimicrobial compounds, their compositions and their uses.

BACKGROUND

The chemical and medical literature describes compounds that are said to be antimicrobial, i.e., capable of destroying or suppressing the growth or reproduction of microorganisms, such as bacteria. For example, such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981).

The mechanism of action of these antibacterials vary. However, they are generally believed to function in one or more of the following ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. As another example, quinolones act, at least in part, by inhibiting synthesis of DNA, thus preventing the cell from replicating.

The pharmacological characteristics of antimicrobials, and their suitability for any given clinical use, vary. For example, the classes of antimicrobials (and members within a class) may vary in 1) their relative efficacy against different types of microorganisms, 2) their susceptibility to development of microbial resistance and 3) their pharmacological characteristics, such as their bioavailability and biodistribution. Accordingly, selection of an appropriate antibacterial (or other antimicrobial) in a given clinical situation requires analysis of many factors, including the type of organism involved, the desired method of administration, the location of the infection to be treated and other considerations.

However, many such attempts to produce improved antimicrobials yield equivocal results. Indeed, few antimicrobials are produced that are truly clinically-acceptable in terms of their spectrum of antimicrobial activity, avoidance of microbial resistance, and pharmacology. Thus there is a continuing need for broad spectrum antimicrobials, which are effective against resistant microbes.

Some 1,4-dihydroquinolone, naphthyridine or related heterocyclic moieties are known in the art to have antimicrobial activity and are described in the following references: R. Albrecht, *Prog. Drug Research*, Vol. 21, p. 9 (1977); J. Wolfson et al., "The Fluoroquinolones: Structures, Mechanisms of Action and Resistance, and Spectra of Activity In Vitro", *Antimicrob. Agents and Chemother.*, Vol. 28, p. 581 (1985); G. Klopman et al., *Antimicrob. Agents and Chemother.*, Vol. 31, p. 1831 (1987); M. P. Wentland et al., *Ann. Rep. Med. Chem.*, Vol. 20, p. 145 (1986); J. B. Cornett et al., *Ann. Rep. Med. Chem.*, Vol. 21, p. 139 (1986); P. B. Fernandes et al., *Ann. Rep. Med. Chem.*, Vol. 22, p. 117 (1987); A. Koga, et al., "Structure-Activity Relationships of Antibacterial 6,7- and 7,8-Disubstituted 1-alkyl-1,4-dihydro-4-oxoquinoline-3-carboxylic Acids", *J. Med. Chem.*, Vol. 23, pp. 1358–1363 (1980); J. M. Domagala et al., *J. Med. Chem.*, Vol. 31, p. 991 (1988); T. Rosen et al., *J. Med. Chem.*, Vol. 31, p. 1586 (1988); T. Rosen et al., *J. Med. Chem.*, Vol. 31, p. 1598 (1988); B. Ledoussal et al., "Non 6-Fluoro Substituted Quinolone Antibacterials: Structure and Activity", *J. Med Chem.*, Vol. 35, p. 198–200 (1992); J. M. Domagala et al., "Quinolone Antibacterials Containing the New 7-[3-(1-Aminoethyl)-1-pyrrolidinyl] Side Chain: The Effects of the 1-Aminoethyl Moiety and Its Stereochemical Configurations on Potency and in Vivo Efficacy", *J. Med. Chem.*, Vol. 36, pp. 871–882 (1993); Hagen et al., "Synthesis and Antibacterial Activity of New Quinolones Containing a 7-[3-(1-Amino-1-methylethyl)-1-pyrrolidinyl] Moiety. Gram Positive Agents with Excellent Oral Activity and Low Side-Effect Potential",*J. Med. Chem.* Vol. 37, pp. 733–738 (1994); V. Cecchetti et al., "Studies on 6-Aminoquinolines: Synthesis and Antibacterial Evaluation of 6-Amino-8-methylquinolones", *J. Med. Chem.*, Vol. 39, pp. 436–445 (1996); V. Cecchetti et al., "Potent 6-Desfluoro-8-methylquinolones as New Lead Compounds in Antibacterial Chemotherapy", *J. Med. Chem.*, Vol. 39, pp. 4952–4957 (1996); Hong et al., "Novel 5-Amino-6-methylquinolone Antibacterials: a New Class of Non-6-fluoroquinolones", *Bioorg. of Med. Chem. Let.*, Vol. 7, pp. 1875–1878 (1997); U.S. Pat. No. 4,844,902 to Grohe on Jul. 4, 1989; U.S. Pat. No. 5,072,001 to Hagen & Suto on Dec. 10, 1991; U.S. Pat. No. 5,328,908 to Demuth & White on Jul. 12, 1994; U.S. Pat. No. 5,457,104 to Bartel et al. on Oct. 10, 1995; U.S. Pat. No. 5,556,979 to Philipps et al. on Sep. 17, 1996; European Patent Appl. 572,259 of Ube Ind. pub. Dec. 1, 1993; European Patent Appl. 775,702 of Toyama Chem. Co. pub. May 28, 1997; Japanese Patent Pub. 62/255, 482 of Kyorin Pharm. Co. pub. Mar. 1, 1995. Additionally, there is a small body of literature describing 2-pyridones, including: European Patent Application No. 308,019 to Heck James, V. et al, Sep. 9, 1988; World Patent Application No. 99/07696 to Tae Ho et al, Aug. 9, 1997; World Patent Application No. 91/16894 to Chu Daniel, T. et al, May 2, 1990; World Patent Application No. 95/10519 to Chu Daniel, T. et al, Oct. 14, 1993; U.S. Pat. No. 5,599,816 to Chu Daniel, T. et al, Jun. 7, 1995; U.S. Pat. No. 5,726,182 to Chu Daniel, T. et al, Jun. 7, 1995; U.S. Pat. No. 5,580,872 to Chu Daniel, T. et al, Sep. 30, 1995; and J. Med. Chem., Vol. 39, pp. 3070–3088 (1996), Qun et al., "Synthesis and Structure-Activity Relationships of 2-Pyridones: A Novel series of Potent DNA Gyrase Inhibitors as Antibacterial Agents."

Examples of bacterial infections resistant to antibiotic therapy have been reported in the past; they are now a significant threat to public health in the developed world. The development of microbial resistance (perhaps as a result of the intense use of antibacterials over extended periods of time) is of increasing concern in medical science. "Resistance" can be defined as existence of organisms, within a population of a given microbial species, that are less susceptible to the action of a given antimicrobial agent. This resistance is of particular concern in environments such as hospitals and nursing homes, where relatively high rates of infection and intense use of antibacterials are common. See, e.g., W. Sanders, Jr. et al., "Inducible Beta-lactamases: Clinical and Epidemiologic Implications for Use of Newer Cephalosporins", *Reviews of Infectious Diseases*, p. 830 (1988).

Pathogenic bacteria are known to acquire resistance via several distinct mechanisms including inactivation of the antibiotic by bacterial enzymes (e.g., β-lactamases hydrolyzing penicillin and cephalosporins); removal of the antibiotic using efflux pumps; modification of the target of the antibiotic via mutation and genetic recombination (e.g., penicillin-resistance in *Neiserria gonorrhoeae*); and acquisition of a readily transferable gene from an external source to create a resistant target (e.g., methicillin-resistance in *Staphylococcus aureus*). There are certain Gram positive pathogens, such as vancomycin-resistant *Enterococcus faecium*, which are resistant to virtually all commercially available antibiotics.

Hence, existing antibacterials have limited capacity in overcoming the threat of resistance. Thus it would be advantageous to provide compounds with useful properties that can be used against resistant microbes.

SUMMARY OF THE INVENTION

Applicants have found a novel series of 2-pyridone compounds that are effective against resistant microbes. In particular, the invention relates to compounds having a structure according to Formula (I)

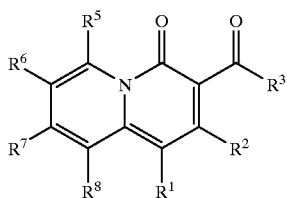

wherein:

(A)
(1) $R^1$ is selected from $C_3$ to about $C_6$ cycloalkyl, $C_4$ to about $C_6$ heterocycloalkyl, lower alkyl, lower alkene, a 6-membered aryl, and a 6-membered heteroaryl;
(2) $R^2$ is hydrogen;
(3) $R^3$ is selected from hydrogen and hydroxy;
(4) $R^5$ is selected from hydrogen, hydroxy, amino, halo, lower alkyl, lower alkene, and lower alkoxy;
(5) $R^6$ is selected from hydrogen, hydroxy, aminocarbonyl, cyano, $C_1$ to about $C_4$ alkyl, and $C_2$ to about $C_4$ alkene; all such alkyl and alkene moieties being unsubstituted or substituted with from 1 to about 3 fluoro, or in the case of methyl or ethyl, optionally substituted with one hydroxy or one amino moiety;
(6) $R^7$ is selected from

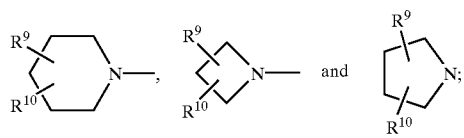

wherein
(a) $R^9$ is (i) amino which is attached to a ring carbon of $R^7$ which is not adjacent to the ring nitrogen of $R^7$, the amino being unsubstituted or substituted with one or two $C_1$ to about $C_3$ alkyl; or (ii) aminoalkyl which is attached to any ring carbon of $R^7$ and is $C_1$ to about $C_3$ alkyl substituted with one amino, the amino being unsubstituted or substituted with one or two $C_1$ to about $C_3$ alkyl; and
(b) $R^{10}$ represents the moieties on $R^7$ other than $R^9$ and each $R^{10}$ is independently selected from hydrogen, $C_1$ to about $C_4$ alkyl, $C_2$ to about $C_6$ alkene, and a $C_3$ to about $C_6$ fused or spirocycle alkyl ring; all alkyl, alkene and cyclic $R^{10}$ moieties being unsubstituted or substituted with one hydroxy or with from 1 to about 3 fluoro moieties; and
(7) $R^8$ is selected from hydrogen, halo, $C_1$ to about $C_2$ alkoxy, $C_1$ to about $C_2$ alkylthio, $C_2$ to about $C_4$ alkyl and lower alkene; or (B) $R^8$ and $R^1$ can join to form a 6-membered heterocyclic ring, where $R^2$, $R^3$, $R^5$, $R^6$ and $R^7$ are as described in (A);

or an optical isomer, diastereomer or enantiomer thereof; or a pharmaceutically-acceptable salt, hydrate, or biohydrolyzable ester, amide or imide thereof. In addition, compounds incorporating the compounds of the invention, or the use of compounds of the invention as starting materials for making other antimicrobial compounds, are also contemplated in this invention.

DESCRIPTION OF THE INVENTION

I. Terms and Definitions

The following is a list of definitions for terms used herein:

"Acyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Alkylthio" is a sulfur radical having a hydrocarbon chain substituent, where the hydrocarbon chain is an alkyl (e.g., —S—$CH_3$) or alkenyl (e.g., —S—$CH_2CH=CH_2$).

"Amino" refers to a primary (—$NH_2$), secondary (—NH (alkyl), also referred to herein as "alkylamino") or tertiary (—N(alkyl)$_2$, also referred to herein as "dialkylamino").

"Aminoalkyl" is an alkyl moiety substituted with an amino, alkylamino or dialkylamino group (e.g., —$CH_2NH_2$, —$CH_2CH_2NH_2$, —$CH_2NHCH_3$, —$CH_2N(CH_3)_2$).

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Biohydrolyzable amides" are aminoacyl, acylamino, or other amides of the compounds of the invention, where the amide does not essentially interfere, preferably does not interfere, with the activity of the compound, or where the amide is readily converted in vivo by a host to yield an active compound.

"Biohydrolyzable imides" are imides of compounds of the invention, where the imide does not essentially interfere, preferably does not interfere, with the activity of the compound, or where the imide is readily converted in vivo by a host to yield an active compound. Preferred imides are hydroxyimides.

"Biohydrolyzable esters" are esters of compounds of the invention, where the ester does not essentially interfere, preferably does not interfere, with the antimicrobial activity of the compound, or where the ester is readily converted in a host to yield an active compound. Many such esters are known in the art, as described in U.S. Pat. No. 4,783,443, issued to Johnston and Mobashery on Nov. 8, 1988 (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkylacylaminoalkyl esters (such as acetamidomethyl esters).

"Carbocyclic ring" encompasses both cycloalkyl and aryl moieties, as those terms are defined herein.

"Carbonyl" is —C(=O)—.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered cycloalkyl rings fused to 5-, 6-, or 7-membered cycloalkyl rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, or heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$–$C_{12}$ haloalkyls; more preferred are $C_1$–$C_6$ haloalkyls; still more preferred still are $C_1$–$C_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, or cyano, or any combination thereof.

"Heteroaryl" is an aromatic ring containing carbon atoms and from 1 to about 6 heteroatoms in the ring. Heteroaryl rings are monocyclic or fused bicyclic ring systemns. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, or heteroaryloxy, or any combination thereof. Preferred heteroaryl rings include, but are not limited to, the following:

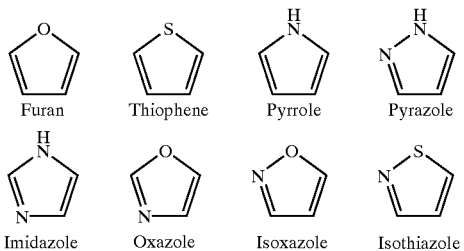

Furan  Thiophene  Pyrrole  Pyrazole

Imidazole  Oxazole  Isoxazole  Isothiazole

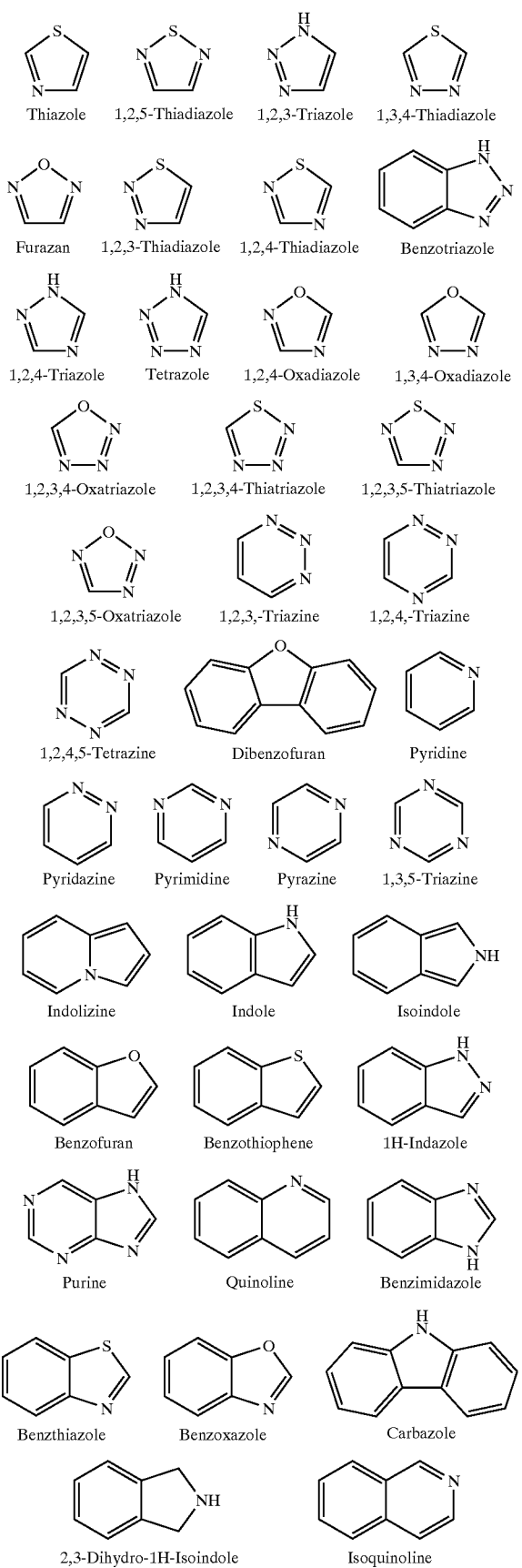
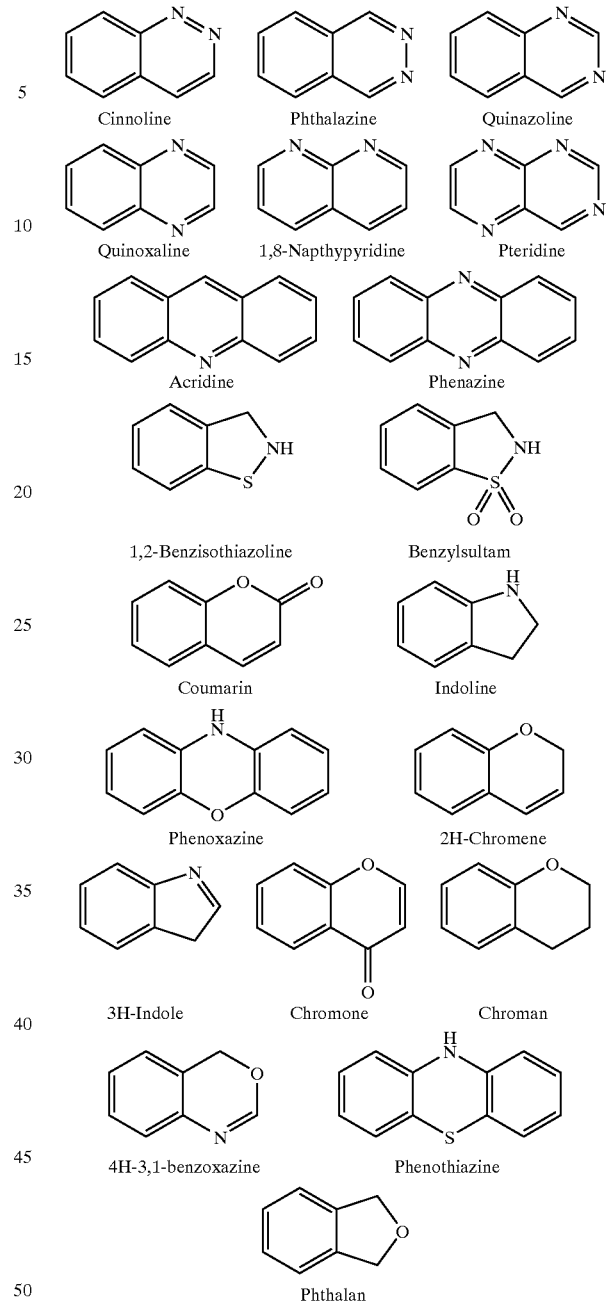

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic or bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms.

Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, or aryloxy, or any combination thereof. Preferred substituents on heterocycloalkyl include halo and haloalkyl. Preferred heterocycloalkyl rings include, but are not limited to, the following:

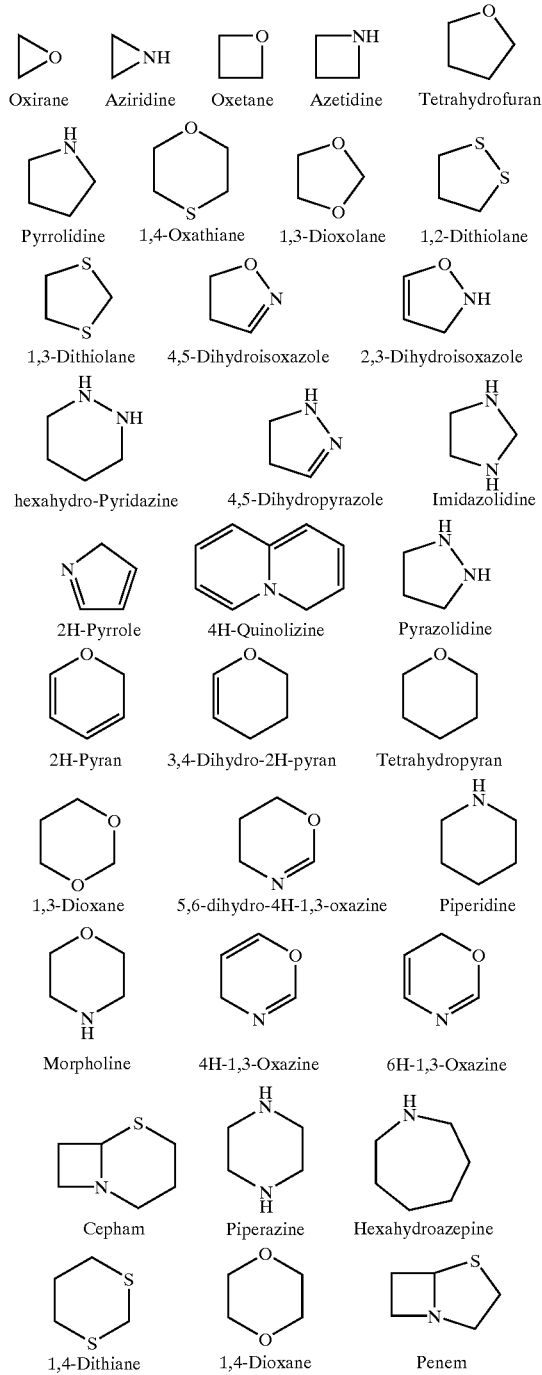

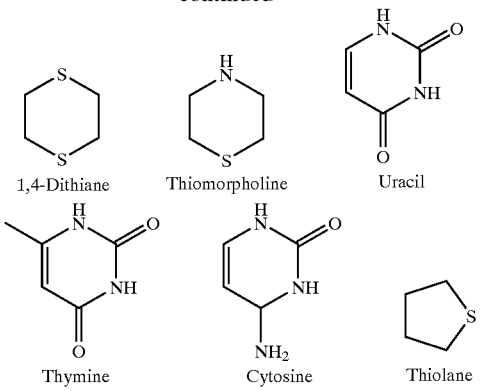

"Heterocyclic ring" encompasses both hetercycloalkyl and heteroaryl moieties, as those terms are defined herein.

"Host" is a substrate capable of sustaining a microbe, typically it is a living organism, more typically an animal, more typically a mammal, more typically still a human.

"Lower" alkoxy, alkylthio, alkyl, alkene or alkyne moiety (e.g., "lower alkyl") is a chain comprised of 1 to 6, preferably from 1 to 4, carbon atoms in the case of alkyl, alkoxy and alkylthio, and 2 to 6, preferably 2 to 4, carbon atoms in the case of alkene and alkyne.

The terms "optical isomer", "stereoisomer", and "diastereomer" have the standard art recognized meanings (see, e.g., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

The compounds of the invention may have one or more chiral centers. As a result, one may selectively prepare one optical isomer, including diastereomer and enantiomer, over another, for example by use of chiral starting materials, catalysts or solvents, one may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers, they may be separated using known methods, such as chiral resolution, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

A "pharmaceutically-acceptable salt" is a cationic salt formed at any acidic (e.g., carboxyl) group, or an anionic salt formed at any basic (e.g., amino, alkylamino, dialkylamino, morpholino, and the like) group on the compound of the invention. Since many of the compounds of the invention are zwitterionic, either salt is possible and acceptable. Many such salts are known in the art. Preferred cationic salts include the alkali metal salts (such as sodium and potassium), alkaline earth metal salts (such as magnesium and calcium) and organic salts, such as ammonio. Preferred anionic salts include halides, sulfonates, carboxylates, phosphates, and the like. Clearly contemplated in such salts are addition salts that may provide an optical center, where there previously were none. For example, a chiral tartrate salt may be prepared from the compounds of the invention, and this definition includes such chiral salts. Salts contemplated are nontoxic in the amounts administered to the patient-animal, mammal or human.

The compounds of the invention are sufficiently basic to form acid-addition salts. The compounds are useful both in the free base form and the form of acid-addition salts, and both forms are within the purview of the invention. The acid-addition salts are in some cases a more convenient form for use. In practice, the use of the salt form inherently amounts to the use of the base form of the active. Acids used to prepare acid-addition salts include preferably those which produce, when combined with the free base, medicinally acceptable salts. These salts have anions that are relatively innocuous to the animal organism, such as a mammal, in medicinal doses of the salts so that the beneficial property inherent in the free base are not vitiated by any side effects ascribable to the acid's anions.

Examples of appropriate acid-addition salts include, but are not limited to, hydrochloride, hydrobromide, hydroiodide, sulfate, hydrogensulfate, acetate, trifluoroacetate, nitrate, citrate, fumarate, formate, stearate, succinate, maleate, malonate, adipate, glutarate, lactate, propionate, butyrate, tartrate, methanesulfonate, trifluoromethanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds are prepared by several methods. For example, the free base can be dissolved in an aqueous alcohol solution containing the appropriate acid and the salt is isolated by evaporation of the solution. Alternatively, they may be prepared by reacting the free base with an acid in an organic solvent so that the salt separates directly. Where separation of the salt is difficult, it can be precipitated with a second organic solvent, or can be obtained by concentration of the solution.

Although medicinally acceptable salts of the basic compounds are preferred, all acid-addition salts are within the scope of the present invention. All acid-addition salts are useful as sources of the free base form, even if the particular salt per se is desired only as an intermediate product. For example, when the salt is formed only for purposes of purification or identification, or when it is used as an intermediate in preparing a medicinally acceptable salt by ion exchange procedures, these salts are clearly contemplated to be a part of this invention.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "solvate" is a complex formed by the combination of a solute (e.g., a 2-pyridone) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the 2-pyridone or 2-pyridone derivative (e.g., water, ethanol, acetic acid, N,N-dimethylformamide and others known or readily determined by the skilled artisan).

"Spirocycle" is an alkyl or heteroalkyl diradical substituent of alkyl or heteroalkyl wherein said diradical substituent is attached geminally and wherein said diradical substituent forms a ring, said ring containing 4 to 8 member atoms (carbon or heteroatom), preferably 5 or 6 member atoms.

While alkyl, heteroalkyl, cycloalkyl, and heterocycloalkyl groups may be substituted with hydroxy, amino, and amido groups as stated above, the following are not envisioned in the invention:

1. Enols (OH attached to an alkene carbon).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

The illustration of specific protected forms and other derivatives of the Formula (I) compounds is not intended to be limiting. The application of other useful protecting groups, salt forms, etc. is within the ability of the skilled artisan.

As used herein, a 2-pyridone derivative includes prodrugs of a 2-pyridone, or an active drug made from a 2-pyridone. Preferably, such derivatives include lactams (e.g., cephems, carbacephems, penems, monolactams, etc.) covalently linked to the 2-pyridone optionally via a spacer. Such derivatives and methods to make and use them are apparent to the skilled artisan, given the teachings of this specification.

II. Compounds: The subject invention invention involves compounds of Formula (I):

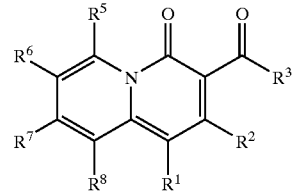

(I)

wherein $R^1$, $R^2$, $R^3$, $R^5$, $R^6$, $R^7$ and $R^8$ are as defined in the Summary of the Invention section above.

With reference to Formula (I), the description above indicates that in one embodiment (defined in sub-part (A)), the nucleus of the compounds will include only two fused rings as depicted. Alternatively, the nucleus will include three fused rings, as defined in sub-part (B) which is depicted as Formula (B) below.

With respect to each of the preferred embodiments described, a non-limiting list of preferred compounds is also set forth in tabular form. It will be recognized that for purification, administration and the like, salts and other derivatives of the above compounds are often used. Thus, a pharmaceutically-acceptable salt, hydrate, or biohydrolyzable ester, amide or imide thereof is contemplated as part of the subject invention and is meant to be included in the tables.

Table I contains a non-limiting list of preferred compounds of Formula (I) where $R^1$ and $R^8$ do not join to form a third fused ring (i.e., compounds of sub-part (A)).

TABLE 1
| R¹ | R² | R³ | R⁵ | R⁶ | R⁷ | R⁸ |
|---|---|---|---|---|---|---|
| Et | H | OH | H | H | 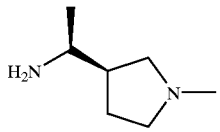 | OMe |
| Et | H | OH | H | H | 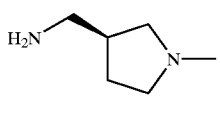 | OMe |
| Et | H | OH | H | H | 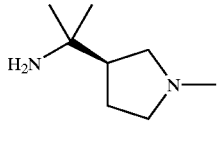 | OMe |
| Et | H | OH | H | H | 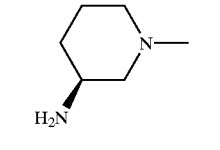 | OMe |
| Et | H | OH | H | H | 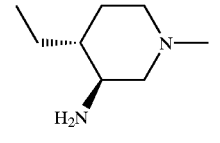 | OMe |
|  | H | OH | H | H | 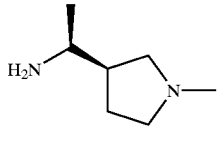 | OMe |
|  | H | OH | H | H |  | OMe |
|  | H | OH | H | H | 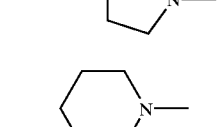 | OMe |
|  | H | OH | H | H | 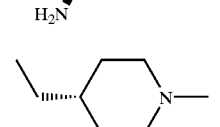 | OMe |
|  | H | OH | H | H | 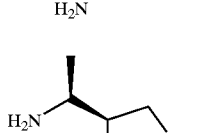 | OMe |
|  | H | OH | H | H |  | OMe |
TABLE 1-continued
| R¹ | R² | R³ | R⁵ | R⁶ | R⁷ | R⁸ |
|---|---|---|---|---|---|---|
|  | H | OH | H | H | 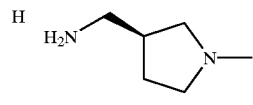 | OMe |
|  | H | OH | H | H | 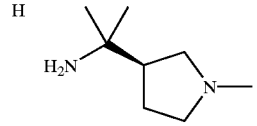 | OMe |
|  | H | OH | H | H | 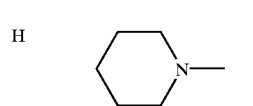 | OMe |
|  | H | OH | H | H | 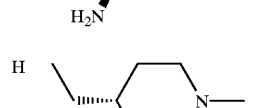 | OMe |
| Et | H | OH | H | H |  | Me |
| Et | H | OH | H | H | 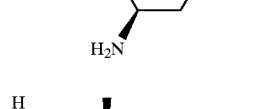 | Me |
| Et | H | OH | H | H |  | Me |
| Et | H | OH | H | H | 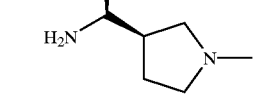 | Me |
| Et | H | OH | H | H |  | Me |
| 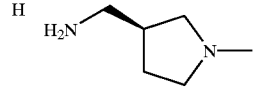 | H | OH | H | H |  | Me |
| 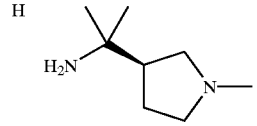 | H | OH | H | H | 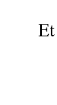 | Me |

TABLE 1-continued
| R¹ | R² | R³ | R⁵ | R⁶ | R⁷ | R⁸ |
|---|---|---|---|---|---|---|
|  | H | OH | H | H |  | Me |
|  | H | OH | H | H |  | Me |
|  | H | OH | H | H |  | Me |
|  | H | OH | H | H |  | Me |
|  | H | OH | H | H |  | Me |
|  | H | OH | H | H |  | Me |
|  | H | OH | H | H |  | Me |
|  | H | OH | H | H |  | Me |
| Et | H | OH | H | H |  | Cl |
| Et | H | OH | H | H |  | Cl |
| Et | H | OH | H | H |  | Cl |
TABLE 1-continued
| R¹ | R² | R³ | R⁵ | R⁶ | R⁷ | R⁸ |
|---|---|---|---|---|---|---|
| Et | H | OH | H | H |  | Cl |
| Et | H | OH | H | H |  | Cl |
|  | H | OH | H | H |  | Cl |
|  | H | OH | H | H |  | Cl |
|  | H | OH | H | H |  | Cl |
|  | H | OH | H | H |  | Cl |
|  | H | OH | H | H |  | Cl |
|  | H | OH | H | H |  | Cl |
|  | H | OH | H | H |  | Cl |
|  | H | OH | H | H |  | Cl |

TABLE 1-continued

| R¹ | R² | R³ | R⁵ | R⁶ | R⁷ | R⁸ |
|---|---|---|---|---|---|---|
| (1-methylcyclopropyl-F) | H | OH | H | H | (3-amino-1-methylpiperidinyl) | Cl |
| (1-methylcyclopropyl-F) | H | OH | H | H | (3-amino-4-ethyl-1-methylpiperidinyl) | Cl |

With regard to Formula (B), the compounds have a structure according to the following structure:

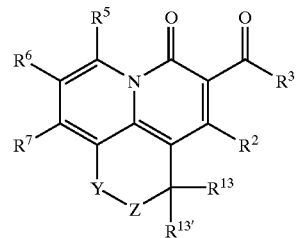

Formula (B)

where $R^1$ and $R^8$ of Formula (I) join to form a 6-membered heterocycloalkyl, and where Y is substituted or unsubstituted —C— or —N— or Y is —O—; $R^{13}$ and $R^{13'}$ are independently selected from hydrogen and lower alkyl; and Z is selected from —O—, —S—, substituted or unsubstituted —C— and substituted or unsubstituted —N—. Preferred for Y is —O—. Preferred for Z is —CH$_2$—. Preferred is where $R^{13}$ is hydrogen and $R^{13'}$ is lower alkyl, preferably methyl.

Table B contains a nonlimiting list of preferred compounds of Formula (B).

TABLE B

| R² | R³ | R⁵ | R⁶ | R⁷ | Y | Z | R¹³ | R¹³' |
|---|---|---|---|---|---|---|---|---|
| H | OH | H | H | (3-aminomethyl-1-methylpyrrolidinyl) | O | CH₂ | H | Me |
| H | OH | H | H | (1-(1-methylpyrrolidin-3-yl)ethylamine) | O | CH₂ | H | Me |
| H | OH | H | H | (2-(1-methylpyrrolidin-3-yl)propan-2-amine) | O | CH₂ | H | Me |
| H | OH | H | H | (3-amino-1-methylpiperidinyl) | O | CH₂ | H | Me |
| H | OH | H | H | (3-amino-4-ethyl-1-methylpiperidinyl) | O | CH₂ | H | Me |
| H | OH | H | H | (3-aminomethyl-1-methylpyrrolidinyl) | S | CH₂ | H | Me |
| H | OH | H | H | (1-(1-methylpyrrolidin-3-yl)ethylamine) | S | CH₂ | H | Me |

TABLE B-continued

| $R^2$ | $R^3$ | $R^5$ | $R^6$ | $R^7$ | Y | Z | $R^{13}$ | $R^{13'}$ |
|---|---|---|---|---|---|---|---|---|
| H | OH | H | H | (pyrrolidinyl with H₂N-C(CH₃)₂-) | S | $CH_2$ | H | Me |
| H | OH | H | H | (piperidinyl with H₂N-) | S | $CH_2$ | H | Me |
| H | OH | H | H | (piperidinyl with H₂N- stereo) | S | $CH_2$ | H | Me |

(Stereochemistry at the carbon atom bearing $R^{13}$ and $R^{13'}$ is preferably the S-configuration)

The preferred compounds of the present invention are those where $R^8$ and $R^1$ do not join to form a ring.

The following provides a description of particularly preferred moieties with respect to each of Formulas (I) and (B), but is not intended to limit the scope of the claims.

$R^1$ is selected from $C_3$ to about $C_6$ cycloalkyl, $C_4$ to about $C_6$ heterocycloalkyl, lower alkyl, lower alkene, a 6-membered aryl, and a 6-membered heteroaryl. Preferred is where $R^1$ is $C_3$ to about $C_6$ cycloalkyl, $C_4$ to about $C_6$ heterocycloalkyl, lower alkyl or lower alkene. Most preferred is $C_3$ to about $C_6$ cycloalkyl and lower alkyl. When $R^1$ is cycloalkyl, preferred are rings having from about 3 to about 5 ring carbon atoms, more preferably 3 ring carbon atoms. $R^1$ cycloalkyl moieties are preferably saturated or unsaturated with one double bond; more preferably cycloalkyl that is saturated. When $R^1$ is linear lower alkyl, preferred is where $R^1$ contains from 1 to about 2 carbon atoms; methyl and ethyl are preferred, most preferred is ethyl. When $R^1$ is lower linear alkene, preferred is where $R^1$ contains from 2 to about 3 carbon atoms; ethenyl is preferred. When $R^1$ is branched lower alkyl or lower alkene, preferred is where $R^1$ contains from 3 to about 4 carbon atoms; branched lower alkyl is preferred; t-butyl is particularly preferred. All of the $R^1$ moieties mentioned in this paragraph are unsubstituted or substituted. When $R^1$ is substituted, preferred is with one or more fluorine atoms. When $R^1$ is a 6-membered aryl or a 6-membered heteroaryl aryl, the ring is unsubstituted or substituted with from 1 to about 3 fluorine atoms, one amino group (preferably at the 3-position of the ring), one hydroxy group (preferably in the 4-position of the ring), or a combination of these substituents; substituted phenyl are preferred. Most preferred $R^1$ moieties are selected from cyclopropyl, ethyl, phenyl substituted with 1 to 3 fluoro, and 4-hydroxyphenyl; more preferred is 2,4-difluorophenyl, and especially cyclopropyl or ethyl.

$R^2$ is hydrogen.

$R^3$ is selected from hydrogen and hydroxy. Preferred is hydroxy. When $R^3$ is hydroxy, it and the carbonyl to which it is attached form a carboxylic acid moiety. As such, it is a potential point of formation for the subject compounds of pharmaceutically-acceptable salts, and biohydrolizable esters, aminoacyls, and amides, as described herein. Compounds having any such variations at the $R^3$ position are included in the subject invention.

$R^5$ is selected from hydrogen, hydroxy, amino, halo, lower alkyl, lower alkene and lower alkoxy. When $R^5$ is lower alkyl, preferred is where $R^5$ has 1 to about 2 carbon atoms, preferably 1 carbon atom. When $R^5$ is lower alkene preferred is where $R^5$ contains from 2 to about 3 carbon atoms, more preferred is where $R^5$ has 2 carbon atoms. When $R^5$ is lower alkoxy, preferred is where $R^5$ has 1 to about 2 carbon atoms, preferably 1 carbon atom. All $R^5$ alkyl, alkene and lower alkoxy moieties are unsubstituted or substituted with fluoro moieties. Preferred $R^5$ is selected from hydrogen, hydroxy, chloro, bromo, amino (preferably —$NH_2$), methyl, monofluoromethyl, difluoromethyl and trifluoromethyl. More preferred $R^5$ is selected from hydrogen, hydroxy, amino, and methyl; most preferred is hydrogen.

$R^6$ is selected from hydrogen, hydroxy, aminocarbonyl, cyano, $C_1$ to about $C_4$ alkyl, and $C_2$ to about $C_4$ alkene, all such alkyl and alkene moieties being unsubstituted or substituted with from 1 to about 3 fluoro, or in the case of methyl or ethyl, optionally substituted with one hydroxy or one amino moiety. $R^6$ alkyl moieties preferably have from 1 to about 2 carbon atoms; preferred are methyl and ethyl; more preferred is methyl. $R^6$ alkenyl moieties have from 2 to about 4 carbon atoms, preferably 2 carbon atoms, with one double bond; ethenyl is preferred. All $R^6$ alkyl moieties are unsubstituted or substituted with from 1 to about 3 fluoro. $R^6$ methyl or ethyl moieties are optionally substituted with one hydroxy moiety or one amino moiety. Preferred $R^6$ is selected from hydrogen, hydroxy, methyl, monofluoromethyl, difluoromethyl, and trifluoromethyl. More preferred $R^6$ is hydrogen.

$R^7$ is selected from

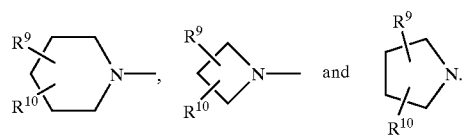

Preferred $R^7$ moieties are pyrrolidinyl and piperidinyl rings.

With respect to $R^7$, $R^9$ is (i) amino which is attached to a ring carbon of $R^7$ which is not adjacent to the ring nitrogen of $R^7$, the amino being unsubstituted or substituted with one or two $C_1$ to about $C_3$ alkyl; or (ii) aminoalkyl which is attached to any ring carbon of $R^7$ and is $C_1$ to about $C_3$ alkyl substituted with one amino, the amino being unsubstituted or substituted with one or two $C_1$ to about $C_3$ alkyl.

When $R^9$ is amino, it is unsubstituted or substituted with one or two alkyl moieties having from 1 to about 3 carbon atoms, preferably methyl or ethyl, more preferably methyl; preferred amino is unsubstituted or substituted with one such alkyl moiety. When $R^7$ is a piperidinyl ring, $R^9$ is preferably an unsubstituted or substituted amino moiety, more preferably at the 3-position. More preferred $R^9$, especially when $R^7$ is a piperidinyl ring, is —$NH_2$.

When $R^9$ is aminoalkyl, the alkyl has from 1 to about 3 carbon atoms, and preferably is methyl, ethyl, or isopropyl. The alkyl is substituted with one amino, such amino being unsubstituted or substituted with 1 or 2, preferably 1, alkyl group having from 1 to about 3 carbon atoms, preferably ethyl or especially methyl. Such aminoalkyl can be attached to any carbon of the ring of $R^7$; preferably it is attached to a carbon not adjacent to the ring nitrogen atom.

$R^9$ is preferably aminoalkyl if $R^7$ is a pyrrolidinyl ring. Preferred $R^9$, especially when $R^7$ is a pyrrolidinyl ring, is selected from aminomethyl, methylaminomethyl, 1-aminoethyl, 1-methylaminoethyl, 1-amino-1-methylethyl, and 1-methylamino-1-methylethyl; such moieties are preferably attached at the 3-position of the pyrrolidinyl ring.

The amino moiety of $R^9$ is a potential point of formation for the subject compounds of a pharmaceutically-acceptable anionic salt; such salts are included in the subject invention compounds. Preferred salts are acid addition salts with, for example, HCl, $CH_3SO_3H$, HCOOH, or $CF_3COOH$.

$R^{10}$ represents the moieties on $R^7$ other than $R^9$ and each $R^{10}$ is independently selected from hydrogen, $C_1$ to about $C_4$ alkyl, $C_2$ to about $C_6$ alkene, and a $C_3$ to about $C_6$ fused or spirocycle alkyl ring. Alkyl $R^{10}$ may be mono- or disubstituents on each ring carbon atom to which $R^9$ is not attached or mono-substituents on the ring carbon to which $R^9$ is attached (i.e., each ring carbon of $R^7$ may have two hydrogens, one hydrogen and $R^9$, one hydrogen and one alkyl, one alkyl and $R^9$, or two alkyls bonded to it). Preferably no more than two ring carbons have alkyl $R^{10}$ substituents; more preferably only one ring carbon has alkyl $R^{10}$ substituents; also preferably all $R^{10}$ are hydrogen. A non-hydrogen, non-alkyl $R^{10}$ (aryl, heteroaryl, hydroxy or alkoxy) may optionally be a mono-substituent on a ring carbon to which $R^9$ is not attached. Preferably there is no more than one non-hydrogen, non-alkyl $R^{10}$ for a subject compound; more preferably there are none.

Non-hydrogen $R^{10}$ includes $C_3$ to about $C_6$ carbocycloalkyl and linear or branched alkyl, preferably linear, having from 1 to about 4 carbon atoms; methyl and ethyl are preferred; methyl is more preferred. Non-hydrogen $R^{10}$ also includes linear or branched alkenyl, preferably linear, having from 2 to about 6 carbon atoms, preferably from 2 to about 4 carbon atoms; ethenyl is preferred. Non-hydrogen $R^{10}$ includes hydroxy and linear or branched alkoxy having from 1 to about 4 carbon atoms, preferably methoxy or ethoxy. Non-hydrogen $R^{10}$ includes aryl, preferably phenyl; and heteroaryl, preferably having 5 or 6 ring atoms with one or two, preferably one, heteroatom that is preferably oxygen or sulfur. Preferred are thienyl and furyl.

Alkyl $R^{10}$, especially dialkyl $R^{10}$, are preferably attached to a carbon of the ring of $R^7$ which is adjacent to the ring nitrogen atom, especially when $R^7$ is a pyrrolidinyl ring. A non-hydrogen, non-alkyl $R^{10}$ is preferably attached to a carbon of the ring of $R^7$ which is not adjacent to the ring nitrogen atom. Also preferred, when $R^7$ comprises the piperidinyl ring and $R^9$ is attached to the 3-carbon of the ring, is for one non-hydrogen $R^9$ to be attached to the 4-carbon of the ring.

Two alkyl $R^9$ moieties can be attached together thus forming a fused or a spirocycle alkyl ring with the N-containing ring of $R^7$, the fused or spirocycle ring having from about 3 to about 6 carbon atoms. Such a fused or spirocycle alkyl ring is preferably saturated or unsaturated with one double bond, more preferably saturated. A spirocyclopropyl ring is particularly preferred.

All alkyl and aryl portions of $R^{10}$ moieties are unsubstituted or substituted with one hydroxy moiety or with from 1 to about 3 fluoro moieties, preferably unsubstituted.

More preferred $R^{10}$ is selected from hydrogen, methyl, dimethyl, spirocyclopropyl, and ethyl; more preferred are ethyl, dimethyl, and spirocyclopropyl; and especially hydrogen.

Optionally, an alkyl $R^{10}$ can be connected to $R^9$ thus forming a fused or a spirocycle ring with the N-containing ring of $R^7$, the fused or spirocycle ring having from 2 to about 5 ring carbon atoms and 0 or 1 ring nitrogen atom (from $R^9$). Such fused or spirocycle ring may be a hydrocarbon ring with an amino or aminoalkyl substituent, the amino being from $R^9$; or it may be a heterocyclic ring with the $R^9$ amino nitrogen being a ring nitrogen. Such ring may have one or two alkanyl substituents. Such fused or spirocycle ring is preferably saturated or unsaturated with one double bond; more preferably it is saturated.

Subject compounds having $R^9$ or $R^{10}$ spirocycles are named according to the following numbering system: the numbering starts at the smaller ring, completing around the larger ring which forms a spiro junction, e.g., at carbon 3 when the smaller ring is cyclopropyl as for the following example:

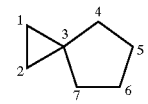

The aza nomenclature used herein follows the conventional nomenclature and is the position where the ring nitrogen is attached to the quinolone nucleus.

$R^8$ is selected from hydrogen, halo, lower alkoxy, lower alkylthio, lower alkyl and lower alkenyl. When $R^8$ is lower alkyl, preferred is where $R^8$ has from 1 to about 2 carbon atoms; methyl is preferred. When $R^8$ is lower alkene, preferred $R^5$ will have from 2 to about 4 carbon atoms; ethenyl is preferred. All $R^8$ alkyl and alkene moieties are unsubstituted or substituted with fluoro. When $R^8$ is lower alkoxy, preferred is where $R^8$ has 1 to about 4 carbon atoms. When $R^8$ is lower alkylthio, preferred is where $R^8$ has 1 to about 4 carbon atoms. Preferred $R^8$ is selected from chloro, methyl, methoxy, methylthio, monofluoromethyl, difluoromethyl, trifluoromethyl, monofluoromethoxy, difluoromethoxy, and trifluoromethoxy. More preferred $R^8$ is selected from methyl substituted with from 1 to 3 fluoro, methoxy, methylthio, and chloro; especially methoxy, methylthio and chloro.

As used herein, any radical is independently selected each time it is used (e.g., $R^1$ and $R^5$ need not be the same in all occurrences in defining a given compound of this invention).

The compounds of the invention may contain chiral center(s), thus any such compound includes and contemplates each optical isomer, diastereomer or enantiomer thereof, in purified or substantially purified form, and mixtures thereof, including racemic mixtures.

The following exemplary compounds are made using the procedures described herein and variations thereof which are within the purview of the skilled artisan's practice. The examples below do not limit the invention, but rather serve to illustrate some of the embodiments of the invention.

The subject invention compounds above are also useful precursors for compounds of formula P—L—B, wherein P is a compound of Formula (I), L is a linking moiety, and B is a lactam containing moiety. This formula includes optical isomers, disatereomers or enantiomers thereof; pharmaceutically-acceptable salts, hydrates, or biohydrolyzable esters, amides and imides thereof. Compounds wherein a quinolone is linked to a lactam and their uses are disclosed in U.S. Pat. No. 5,180,719 issued Jan. 19, 1993; U.S. Pat. No. 5,387,748 issued Feb. 7, 1995; U.S. Pat. No. 5,491,139 issued Feb. 13, 1996; U.S. Pat. No. 5,530,116 issued Jun. 25, 1996; and EPO publications 0366189 published May 2, 1990 and 0366640 published May 2, 1990, all incorporated herein by reference. The skilled artisan will recognize that the 2-pyridone compounds of the present invention can be substituted for the quinolones disclosed in these references. For compositions and methods of use, the compounds of formula P—L—B are useful in the same way as compounds of Formula (I). Thus, they can be interchanged in the composition examples herein.

Biological activities of the invention compounds can be compared to ciprofloxacin and the other known antimicrobial compounds. Compounds of the subject invention provide better antibacterial properties against certain quinolone resistant bacteria compared to ciprofloxacin and certain other prior art compounds. When tested against quinolone-resistant bacteria such as S. aureus, S. saprophyticus, E. faecalis, S. pyogenes, S. pneumoniae, S. viridans, E. coli, P. aeruginosa, P. mirabilis, K. pneumoniae, E. cloacae, certain compounds of the subject invention have been found to have MIC values (µg/ml) that are up to about 500 times lower than ciprofloxacin.

III. General Reaction Schemes for Compound Preparation

In making the compounds of the invention, the order of synthetic steps may be varied to increase yield of desired product. In addition, the skilled artisan will also recognize the judicious choice of reactants, solvents, and temperatures is an important component in successful synthesis. While the determination of optimal conditions, etc. is routine, it will be understood that a variety of compounds can be generated in a similar fashion, using the guidance of the scheme below. Specific synthetic examples are set forth for a variety of compounds in Section VI.

The starting materials used in preparing the compounds of the invention are known, made by known methods, or are commercially available as a starting material.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2), Fieser & Feiser, *Reagents for Organic Synthesis* (16 volumes), L. Paquette, *Encyclopedia of Reagents for Organic Synthesis* (8 volumes), Frost & Fleming, *Comprehensive Organic Synthesis* (9 volumes) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

General procedures for preparing 2-pyridone moieties useful in making the compounds of the subject invention are described in the following references, all incorporated by reference herein (including articles listed within these references): European Patent Application No. 308,019 to Heck James, V. et al, Sep. 9, 1988; World Patent Application No. 99/07696 to Tae Ho et al, Aug. 9, 1997; World Patent Application No. 91/16894 to Chu Daniel, T. et al, May 2, 1990; World Patent Application No. 95/10519 to Chu Daniel, T. et al, Oct. 14, 1993; U.S. Pat. No. 5,599,816 to Chu Daniel, T. et al, Jun. 7, 1995; U.S. Pat. No. 5,726,182 to Chu Daniel, T. et al, Jun. 7, 1995; U.S. Pat. No. 5,580,872 to Chu Daniel, T. et al, Sep. 30, 1995; and *J. Med. Chem.,* Vol. 39, pp. 3070–3088 (1996), Qun et al., "Synthesis and Structure-Activity Relationships of 2-Pyridones: A Novel series of Potent DNA Gyrase Inhibitors as Antibacterial Agents." One methodology for providing the compounds of the invention is shown in Reaction Scheme below:

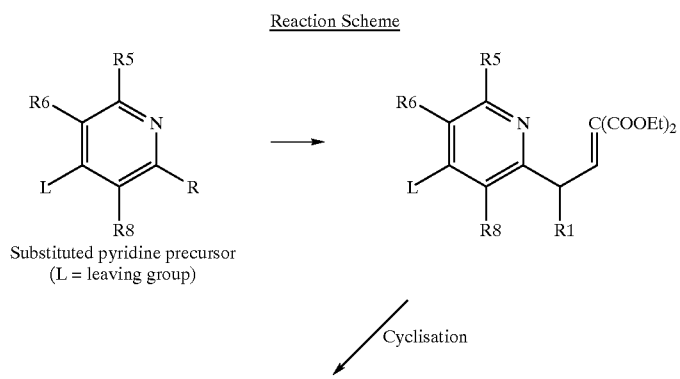

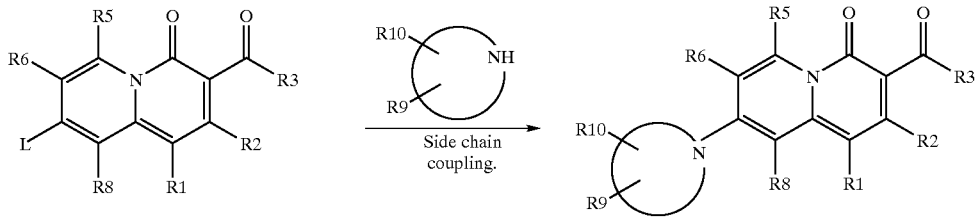

In this reaction scheme, the pyridone nucleus is typically obtained from the corresponding substituted pyridine containing a leaving group at the 4-position for subsequent introduction of the desired side chain.

IV. Compositions

The compositions of this invention comprise:

(a) a safe and effective amount of the compound of the invention; and (b) a pharmaceutically-acceptable excipient.

It may also optionally comprise other antimicrobials or other actives, which may or may not act synergystically with the invention.

A "safe and effective amount" of a 2-pyridone is an amount that is effective, to inhibit microbial growth at the site of an infection to be treated in a host, without undue adverse side effects (such as toxicity, irritation, or allergic response), commensurate with a reasonable benefit/risk ratio when used in the manner of this invention. The specific "safe and effective amount" will vary with such factors as the particular condition being treated, the physical condition of the patient, the duration of treatment, the nature of concurrent therapy (if any), the specific dosage form to be used, the excipient employed, the solubility of the 2-pyridone therein, and the dosage regimen desired for the composition.

The compositions of this invention are preferably provided in unit dosage form. As used herein, a "unit dosage form" is a composition of this invention containing an amount of a 2-pyridone that is suitable for administration to a human or lower animal subject, in a single dose, according to good medical practice. These compositions preferably contain from about 30 mg, more preferably from about 50 mg, more preferably still from about 100 mg, preferably to about 20,000 mg, more preferably to about 7,000 mg, more preferably still to about 1,000 mg, most preferably to about 500 mg, of a 2-pyridone.

The compositions of this invention may be in any of a variety of forms, suitable (for example) for oral, rectal, topical or parenteral administration. Depending upon the particular route of administration desired, a variety of pharmaceutically-acceptable excipients well-known in the art may be used. These include solid or liquid fillers, diluents, hydrotropes, surface-active agents, and encapsulating substances. Optional pharmaceutically-active materials may be included, which do not substantially interfere with the antimicrobial activity of the 2-pyridone. The amount of excipient employed in conjunction with the 2-pyridone is sufficient to provide a practical quantity of material for administration per unit dose of the 2-pyridone. Techniques and compositions for making dosage forms useful in the methods of this invention are described in the following references, all incorporated by reference herein: *Modern Pharmaceutics*, Vol. 7, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In particular, pharmaceutically-acceptable excipients for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred excipients for parenteral administration include propylene glycol, ethyl oleate, pyrrolidone, ethanol, and sesame oil. Preferably, the pharmaceutically-acceptable excipient, in compositions for parenteral administration, comprises at least about 90% by weight by the total composition.

In addition, dosages for injection may be prepared in dried or lyophilized form. Such forms can be reconstituted with water or saline solution, depending on the preparation of the dosage form. Such forms may be packaged as individual dosages or multiple dosages for easier handling. Where lyophilized or dried dosages are used, the reconstituted dosage form is preferably isotonic, and at a physiologically compatible pH.

Various oral dosage forms can be used, including such solid forms as tablets, capsules, granules and bulk powders. These oral forms comprise a safe and effective amount, usually at least about 5%, and preferably from about 25% to about 50%, of the 2-pyridone. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents, such are well known to the skilled artisan. Preferred excipients for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions preferably comprise a safe and effective amount, usually at least about 0.1%, and preferably from about 1% to about 5%, of the 2-pyridone. Suitable excipients for topical administration preferably remain in place on the skin as a continuous film, and resist being removed by perspiration or immersion in water. Generally, the excipient is organic in nature and capable of having dispersed or dissolved therein the 2-pyridone. The excipient may include pharrnaceutically-acceptable emolients, emulsifiers, thickening agents, and solvents and the like; these are well known to the skilled artisan.

V. Methods of Using the Compounds

This invention also provides methods of treating an infectious disorder in a human or other animal subject, by administering a safe and effective amount of a 2-pyridone to said subject. As used herein, an "infectious disorder" is any disorder characterized by the presence of a microbial infection. Preferred methods of this invention are for the treatment of bacterial infections. Such infectious disorders include (for example) central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, including pneumonia, genitourinary infections, gastrointestinal infections, gynecological infections, septicemia, sepsis, peritonitis, bone and joint infections, skin and skin structure infections, bacterial endocarditis, burns, antibacterial prophylaxis of surgery, and antibacterial prophylaxis in postoperative patients or in immunosuppressed patients (such as patients receiving cancer chemotherapy, or organ transplant patients).

The term "treatment" is used herein to mean that, at a minimum, administration of a compound of the present invention mitigates a disease associated an infectious disorder in a host, preferably in a mammalian subject, more preferably in humans. Thus, the term "treatment" includes: preventing an infectious disorder from occurring in a host, particularly when the host is predisposed to acquiring the disease, but has not yet been diagnosed with the disease; inhibiting the infectious disorder; and/or alleviating or reversing the infectious disorder. Insofar as the methods of the present invention are directed to preventing infectious disorders, it is understood that the term "prevent" does not require that the disease state be completely thwarted. (See Webster's Ninth Collegiate Dictionary.) Rather, as used herein, the term preventing refers to the ability of the skilled artisan to identify a population that is susceptible to infectious disorders, such that administration of the compounds of the present invention may occur prior to onset of infection. The term does not imply that the disease state need be completely avoided.

The 2-pyridone derivatives and compositions of this invention can be administered topically or systemically. Systemic application includes any method of introducing the 2-pyridone into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, are mutually dependent. The dosage and treatment regimen will also depend upon such factors as the specific 2-pyridone used, the resistance pattern of the infecting organism to the 2-pyridone used, the ability of the 2-pyridone to reach minimum inhibitory concentrations at the site of the infection, the nature and extent of other infections (if any), the personal attributes of the subject (such as weight), compliance with the treatment regimen, the age and health status of the patient, and the presence and severity of any side effects of the treatment.

Typically, for a human adult (weighing approximately 70 kilograms), from about 75 mg, more preferably from about 200 mg, most preferably from about 500 mg to about 30,000 mg, more preferably to about 10,000 mg, most preferably to about 3,500 mg, of 2-pyridone is administered per day. Treatment regimens preferably extend from about 1, preferably from about 3 to about 56 days, preferably to about 20 days, in duration. Prophylactic regimens (such as avoidance of opportunistic infections in immuno-compromised patients) may extend 6 months, or longer, according to good medical practice.

A preferred method of parenteral administration is through intravenous injection. As is known and practiced in the art, all formulations for parenteral administration must be sterile. For mammals, especially humans, (assuming an approximate body weight of 70 kilograms) individual doses of from about 100 mg, preferably from about 500 mg to about 7,000 mg, more preferably to about 3,500 mg, is acceptable.

In some cases, such as generalized, systemic infections or in immune-compromised patients, the invention may be dosed intravenously. The dosage form is generally isotonic and at physiological pH. The dosage amount will depend on the patient and severity of condition, as well as other commonly considered parameters. Determination of such doses is well within the scope of practice for the skilled practitioner using the guidance given in the specification.

A preferred method of systemic administration is oral administration. Individual doses of from about 20 mg, more preferably from about 100 mg to about 2,500 mg, more preferably to about 500 mg.

Topical administration can be used to deliver the 2-pyridone systemically, or to treat a local infection. The amounts of 2-pyridone to be topically administered depends upon such factors as skin sensitivity, type and location of the tissue to be treated, the composition and excipient (if any) to be administered, the particular 2-pyridone to be administered, as well as the particular disorder to be treated and the extent to which systemic (as distinguished from local) effects are desired.

VI. EXAMPLES

Compound Preparation

The following abbreviations are used herein:

THF: Tetrahydrofuran

LDA: Lithium diisopropylamide

DIBAL: Diisobutyl aluminium hydride a. Precursor Preparation—Nuclei

Precursor Example A

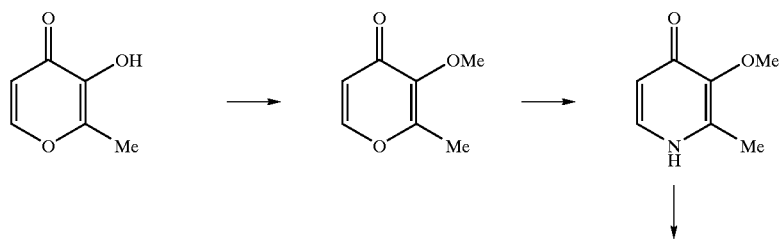

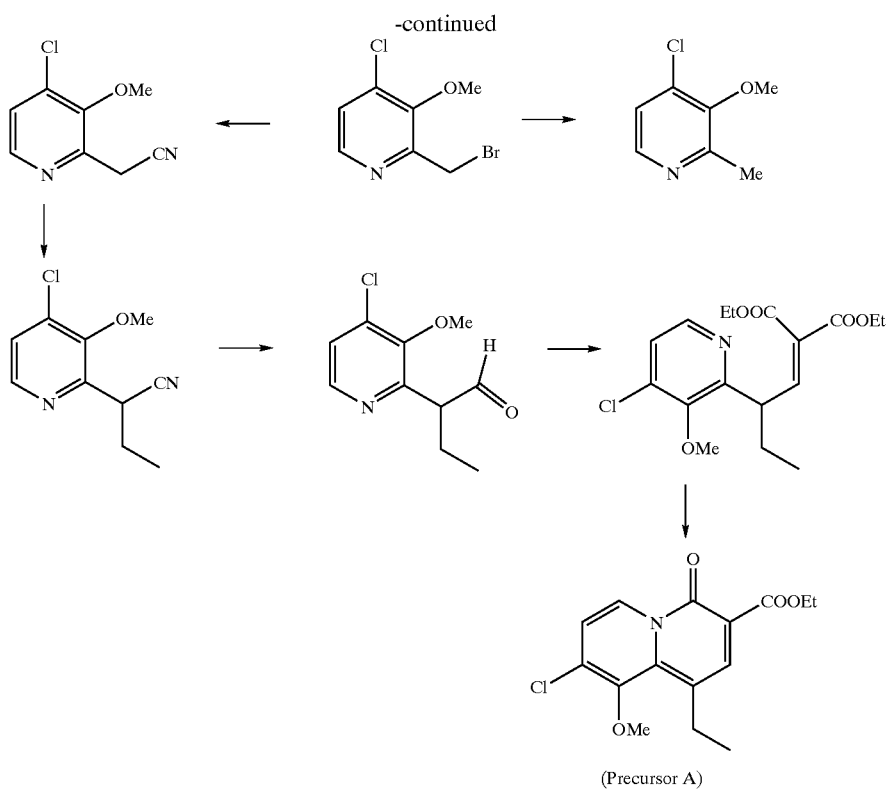

(Precursor A)

3-Methoxy-2-methyl-1,4-pyrone 3-hydroxy-2methyl-1,4pyrone (100.3 g) is dissolved in 500 ml of a 10% solution of KOH in water. Dimethyl sulfate (76 ml) is then added over a period of 30 min, while keeping the temperature around 25° C. The reaction is then concentrated to one quarter of the original volume and acidified by addition of hydrochloric acid. This phase is extracted 3 times with ethyl acetate, the organic phase dried over sodium sulfate and the solvent evaporated to yield the desired product.

3-Methoxy-2-methyl-1,4-pyridone

3-Methoxy-2-methyl-1,4pyrone (64.14 g) is mixed with a 28% aqueous solution of ammonia (750 ml) in a glass lined steel bomb and the mixture is stirred at 120° C. for 24 hours. The excess of water and ammonia is evaporated and the residue triturated in a mixture of ethanol and ethyl acetate; the solid is filtered and dried to afford the desired product.

4-Chloro-3-methoxy-2-methyl-pyridine

3-Methoxy-2-methyl-1,4-pyridone (11.29 g) is mixed in phosphorous oxychloride (100 ml) and refluxed for 10 hours. The excess of reagent is evaporated and the residue is redissolved in toluene (100 ml) and evaporated. Water (100 ml) is added to the residue and the pH adjusted to 11 by addition of potassium carbonate, then extracted with methylene chloride. The organic phased is dried over sodium sulfate and evaporated to afford the desired product.

4-Chloro-3-methoxy-2-bromomethyl-pyridine

4-Chloro-3-methoxy-2-methyl-pyridine (6.12 g) is dissolved in carbon tetrachloride (80 ml) then N-bromosuccinimide (7.12 g) and benzoyl peroxide (1 g) are added. The reaction mixture is refluxed under UV irradiation for 1.5 hour. The solid is filtered after cooling and the solvent evaporated. The desired product is purified by chromatography on silica gel.

2-(4-Chloro-3-methoxy-2-pyridinyl)-acetonitrile

4-Chloro-3-methoxy-2-bromomethyl-pyridine (4.69 g) and sodium cyanide (5.11 g) are added to ml of a 1/1 mixture of water and ethanol. The reaction is stirred at 60° C. for 3 hours. The ethanol is evaporated and the residue diluted in water and extracted with methylene chloride. The desired product is obtained by chromatography using hexane/ethyl acetate (9/1) as solvent.

2-(4-Chloro-3-methoxy-2-pyridinyl)-butyronitrile 2-(4-Chloro-3-methoxy-2-pyridinyl)-acetonitrile (7.06 g) is dissolved in THF (40 ml) and 60% sodium hydride (1.62 g) is added followed by 3.25 ml of ethyl iodide. The reaction is allowed to stir at 45° C. for 1.5 hour then the reaction mixture is diluted with water and extracted with ethyl acetate. The desired product is purified by chromatography using hexane/ethyl acetate 4/1 as solvent.

2-(4-Chloro-3-methoxy-2-pyridinyl)-butanal 2-(4-Chloro-3-methoxy-2-pyridinyl)-butyronitrile (2.78 g) is dissolved in diethyl ether (150 ml), the solution is cooled to −74° C. and DIBAL (29 ml 1.0M) is added over a 30 min period. The solution is allowed to stir at −74° C. for an hour then at 0° C. for another hour. The reaction is quenched by addition of 5% sulfuric acid (25 ml), keeping the temperature around 0° C. The phases are separated and the organic phase washed with a solution of sodium bicarbonate, dried and evaporated to afford the desired product.

Ethyl-4-(4-Chloro-3-methoxy-2-pyridinyl)-2-carboxyethyl-hexen-2-oate 2-(4-Chloro-3-methoxy-2-pyridinyl)-butanal (1.081 g) is dissolved in 40 ml of ethanol. Piperidine (1.2 ml), acetic acid (1.2 ml), and diethyl malonate are then added sequentially. The reaction is stirred at 40° C. overnight and the volatiles removed, the residue is redissolved in ether, washed with water, brine, and evaporated. The desired product is purified by chromatography using hexane/ethyl acetate 4/1 as solvent.

Ethyl-8-chloro-1-ethyl-9-methoxy-4-oxo-4H-quinolizine-3-carboxylate (Precursor A)

Ethyl-4-(4-Chloro-3-methoxy-2-pyridinyl)-2-carboxyethyl-hexen-2-oate (0.624 g) is dissolved in 25 ml of Dowtherm™ and heated at 200° C. for 4 hours. The desired product is purified by chromatography using hexane then ethyl acetate as solvent.

Precursor Example B added. The reaction is stirred at −45° C. for one hour and allowed to warm at room temperature before being quenched by 5 ml of 28% ammonium hydroxide. The reaction is extracted with ether and the desired product purified by chromatography using hexane/ethyl acetate 9/1 as solvent.

Ethyl-4-(4-Chloro-3-methoxy-2-pyridinyl)-4-cyclopropyl-2-carboxyethyl-buten-2-oate A solution of LDA (2.0M, 0.8 ml) is dissolved in 2 ml of THF and the solution cooled at −60° C. A solution of 4-Chloro-3-methoxy-2-(cyclopropyl)-methyl pyridine (0.36 g) in THF (1 ml) is added dropwise, keeping the temperature at −60° C. and the reaction is stirred at the same temperature for one hour. Diethyl (ethoxymethylene)malonate is added and the solution is slowly allowed to warm at room temperature. Water is added and the reaction is extracted with dichloromethane. The desired product is purified by chromatography using hexane ethyl acetate 4/1 as solvent.

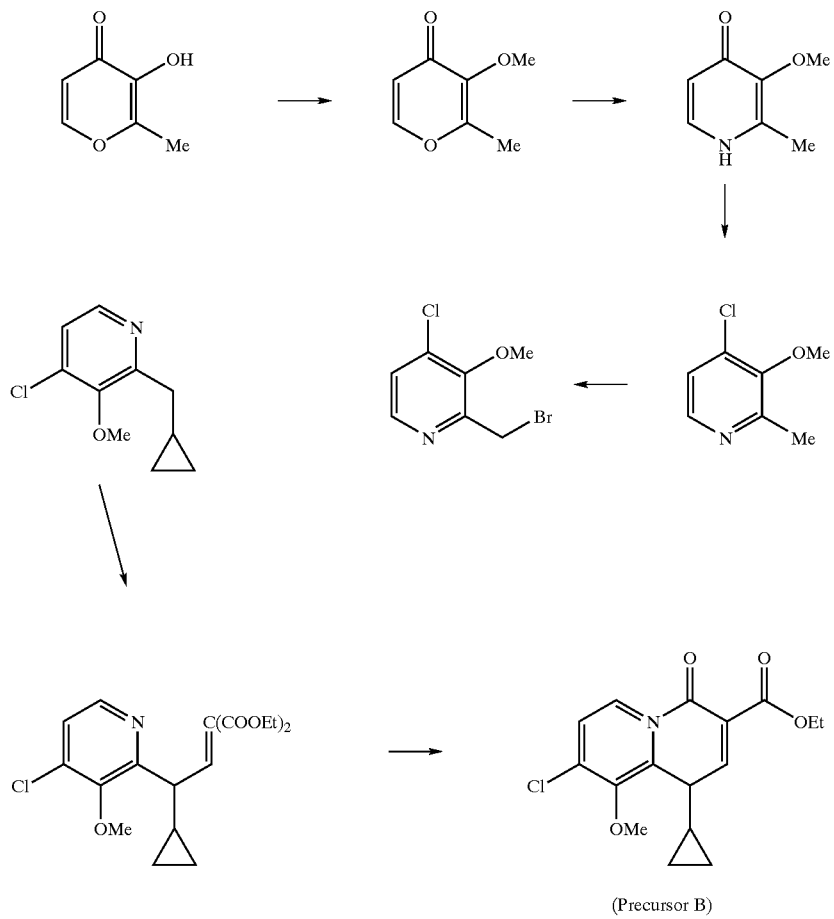

(Precursor B)

4-Chloro-3-methoxy-2-(cyclopropyl)-methyl pyridine

Cyclopropyl bromide (0.5 ml) is dissolved in 5 mnl of THF and magnesium (0.15 g) is added and heat is applied to initiate the reaction. Once the reaction is completed, the solution is cooled to −45° C. and cuprous iodide (0.5 g) is added. The reaction is allowed to stir for 30 minutes and 4-Chloro-3-methoxy-2-bromomethyl-pyridine (0.154 g) is

Ethyl-8-chloro-1-cyclopropyl-9-methoxy-4-oxo-4H-quinolizine-3-carboxylate (Prec. B)

Ethyl-4-(4-Chloro-3-methoxy-2-pyridinyl)-4-cyclopfopyl-2-carboxyethyl-buten-2-oate (0.28 g) is dissolved in 12 ml of Dowtherm™ and heated at 200° C. for 4 hours. The desired product is purified by chromatography using hexane then ethyl acetate as solvent.

Precursor Example C

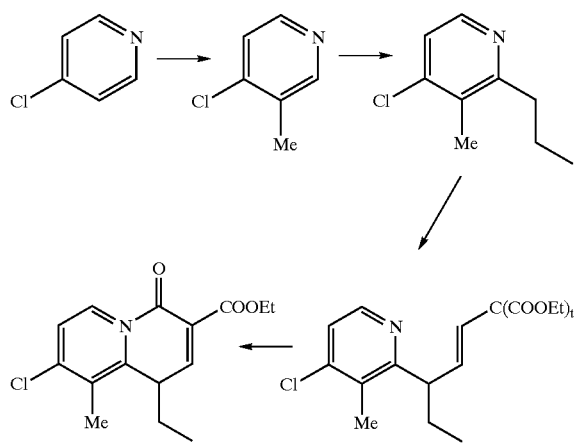

4-Chloro-3-methyl-pyridine

To a solution of LDA (2.0 M, 50 ml) in THF (100 ml) at −70° C. is added 4-chloropyridine (11.3 g) in solution in THF (20 ml) keeping the temperature below −65° C. The reaction is allowed to stir for 4 hours at −70° C. and methyl iodide (15 g) is added keeping the temperature below −65° C. The reaction is then allowed to warm at room temperature and water is added. The aqueous phase is extracted with ether and the desired compound is obtained by distillation under reduced pressure after removal of the solvent.

2-Propyl-4-chloro-3-methyl-pyridine

To a solution of propyl iodide (12.7 g) in THF (10 ml) is added lithium (0.45 g) and the reaction is allowed to stir at room temperature until complete dissolution of the lithium. 4-Chloro-3-methyl-pyridine (9.5 g) is then added and the mixture allowed to stir at 40° C. for 4 hours. After cooling at room temperature, ether is added and the organic phase washed with water. After removal of the solvent the desired product is obtained by chromatography using hexane/ether 9/1 as solvent.

Ethyl-4-(4-Chloro-3-methyl-2-pyridinyl)-2-carboxyethyl-hexen-2-oate

A solution of LDA (2.0M, 5 ml) is dissolved in 20 ml of THF and the solution cooled at −60° C. A solution of 2-propyl-4-chloro-3-methyl-pyridine (1.7 g) in THF (5 ml) is added dropwise, keeping the temperature at −60° C. and the reaction is stirred at the same temperature for one hour. Diethyl (ethoxymethylene)malonate is added and the solution is slowly allowed to warm at room temperature. Water is added and the reaction is extracted with dichloromethane. The desired product is purified by chromatography using hexane/ethyl acetate 4/1 as solvent.

Ethyl-8-chloro-1-ethyl-9-methyl-4-oxo-4H-quinolizine-3-carboxylate (Precursor C)

Ethyl-4-(4-Chloro-3-methyl-2-pyridinyl)-2-carboxyethyl-hexen-2-oate (0.72 g) is dissolved in 20 ml of Dowtherm™ and heated at 200° C. for 4 hours. The desired product is purified by chromatography using hexane then ethyl acetate as solvent.

b. Precursor Preparation—7-Position Moiety

Precursor Example D

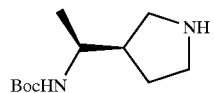

3-(N-boc-aminoethyl)pyrrolidine (Precursor D) is prepared according to *Chem. Pharm. Bull.* 42(7) 1442–1454 (1994) and references cited therein.

Precursor Example E

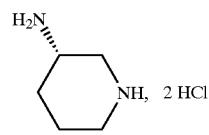

3-S-aminopiperidine dihydrochloride (Precursor E) is prepared according to *J. Chem soc Dalton Trans.* 1127–1132 (1987).

C. Final Product Preparation

General Synthetic Pathway

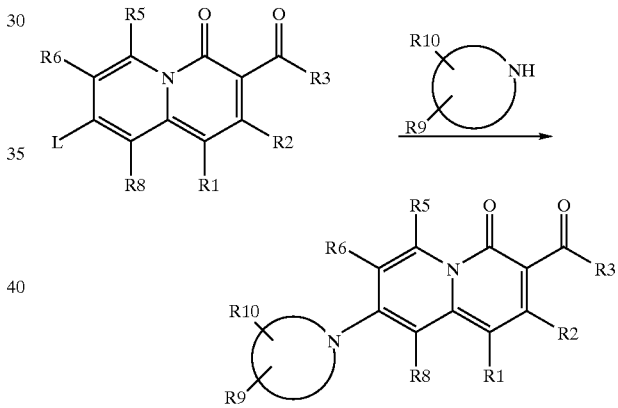

Example 1

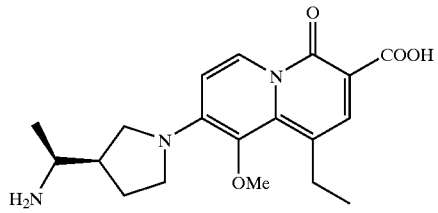

8-[3-(N-boc-aminoethyl)pyrrolidinyl]-1-ethyl-9-methoxy-4-oxo-4H-quinolizine-3-carboxylic acid ethyl ester Ethyl-8-chloro-1-ethyl-9-methoxy-4-oxo-4H-quinolizine-3-carboxylate (Precursor A) (0.151 g) and triethylamine (0.5 ml) are dissolved in acetonitrile (6 ml). To this solution 3-(N-boc-aminoethyl)pyrrolidine (Precursor D) (0.215 g) is added and the solution stirred at 40° C. for 18 hours. The solvent is evaporated and the residue dissolved in dichloromethane, washed with 1N hydrochloric acid and dried over sodium sulfate. The desired product is obtained by evaporation of the solvent.

8-[3-(N-boc-aminoethyl)pyrrolidinyl]-1-ethyl-9-methoxy-4oxo-4H-quinolizine-3carboxylic acid 8-[3-(Nboc-aminoethyl)pyrrolidinyl]-1-ethyl-9-methoxy-4-oxo-4H-quinolizine-3-carboxylic acid ethyl ester (0.234 g) is suspended in a mixture of water/THF (60 ml 5/1) and lithium hydroxide (0.215 g) is added. The reaction is stirred at 60° C. for 36 hours then cooled, acidified to pH 2 by addition of hydrochloric acid and the solution is extracted with dichloromethane. The extracts are dried over sodium sulfate and the solvent evaporated to afford the desired product.

8-[3-aminoethyl-pyrroacdinyl]1-ethyl-9-methoxy-4-oxo-4H-quinodzine-3-carboxylc acid 8-[3-(N-boc-aminoethyl)pyrrolidinyl]-1-ethyl-9-methoxy-4-oxo-4H-quinolizine-3-carboxylic acid (0.12 g) is dissolved in dry dichloromethane (3 ml) and iodotrimethylsilane (0.0534 g) is added. The solution is allowed to stir 5 minutes and ethanol (5 ml) is added. The solution is partially concentrated and the precipitate filtered to afford the title compound.

Example 2

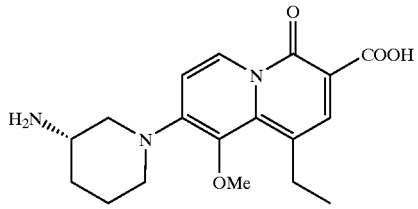

8-(3-aminopiperidinyl)-1-ethyl-9-methoxy-4-oxo-4H-quinolizine-3-carboxylic acid, ethyl ester Ethyl-8-chloro-1-ethyl-9-methoxy-4-oxo-4H-quinolizine-3-carboxylate (Precursor A) (0.05 g) is dissolved in acetonitrile (3 ml) and triethylamine (0.3 ml). To this solution is added 3-S-aminopiperidine dihydrochloride (Precursor E) (0.055 g) and the mixture is stirred at 40° C. for five days. The reaction mixture is evaporated and the desired product obtained by recrystallization in isopropyl alcohol.

8-(3-aminopiperidinyl)-1-ethyl-9-methoxy-4-oxo-4H-quinolizine-3-carboxylic acid 8-(3-aminopiperidinyl)-1-ethyl-9-methoxy-4-oxo-4H-quinolizine-3-carboxylic acid, ethyl ester (0.028 g) is dissolved in 9 ml of a 2/1 mixture of water and THF and lithium hydroxide (0.035 g) is added. The resulting solution is stirred at 60° C. for 4 days and the solution adjusted to pH 7.2 by addition of acetic acid. The title compound is collected by filtration of the precipitate.

Example 3

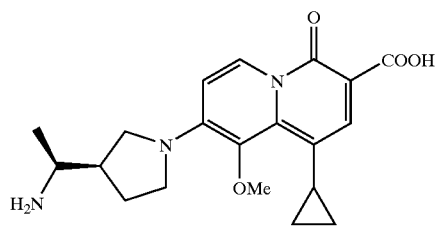

8-[3-aminoethyl-pyrrolidinyl]-1-cyclopropyl-9-methoxy-4-oxo-4H-quinolizine-3-carboxylic acid A series of procedures similar to Example 1 above is carried out, using Ethyl-8-chloro-1-cyclopropyl-9-methoxy-4-oxo-4H-quinolizine-3-carboxylate (Precursor B) and 3-(N-boc-aminoethyl)pyrrolidine (Precursor D) as the starting materials.

Example 4

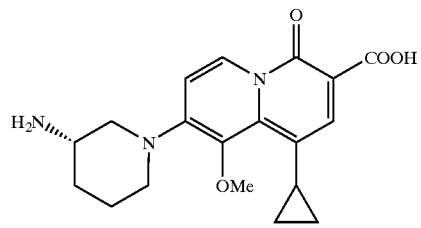

8-(3-aminopiperidinyl)-1-cyclopropyl-9-methoxy-4-oxo-4H-quinolizine-3-carboxylic acid A series of procedures similar to Example 2 above is used using Ethyl-8-chloro-1-cyclopropyl-9-methoxy-4-oxo-4H-quinolizine-3-carboxylate (Precursor B) and 3-S-aminopiperidine dihydrochloride (Precursor E) as the starting materials.

Example 5

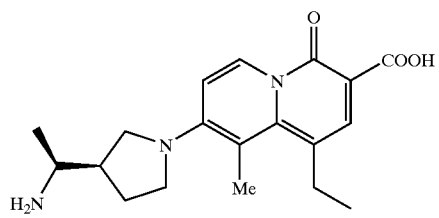

A series of procedures similar to Example 1 above is used using Ethyl-8-chloro-1-ethyl-9-methyl-4-oxo-4H-quinolizine-3-carboxylate (Precursor C) and 3-(N-boc-aminoethyl)pyrrolidine (Precursor D) as the starting materials.

Example 6

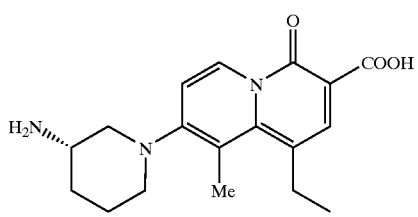

A series of procedures similar to Example 2 above is used using Ethyl-8-chloro-1-ethyl-9-methyl-4-oxo-4H-quinolizine-3-carboxylate (Precursor C) and 3-S-aminopiperidine dihydrochloride (Precursor E) as the starting materials.

VII. EXAMPLES
Compositions and Methods of Use

The following non-limiting examples illustrate the compositions and methods of use of the present invention.

Example 7

A tablet composition for oral administration, according to the present invention, is made comprising:

| Component | Amount |
| --- | --- |
| Compound of Example 1 | 150 mg |
| Lactose | 120 mg |
| Maize Starch | 70 mg |
| Talc | 4 mg |
| Magnesium Stearate | 1 mg |

Other compounds having a structure according to Formula (I) are used with substantially similar results.

Example 8

A capsule containing 200 mg of active for oral administration, according to the present invention, is made comprising:

| Component | Amount (% w/w) |
| --- | --- |
| Compound of Example 4 | 15% |
| Hydrous Lactose | 43% |
| Microcrystalline Cellulose | 33% |
| Crosspovidone | 3.3% |
| Magnesium Stearate | 5.7% |

Other compounds having a structure according to Formula (I) are used with substantially similar results.

Example 9

A saline-based composition for ocular administration, according to the present invention, is made comprising:

| Component | Amount (% w/w) |
| --- | --- |
| Compound of Example 2 | 10% |
| Saline | 90% |

Other compounds having a structure according to Formula (I) are used with substantially similar results.

Example 10

An intranasal composition for local administration, according to the present invention, is made comprising:

| Component | Composition (% w/v) |
| --- | --- |
| Compound of Example 5 | 0.20 |
| Benzalkonium chloride | 0.02 |
| EDTA | 0.05 |
| Glycerin | 2.0 |
| PEG 1450 | 2.0 |
| Aromatics | 0.075 |
| Purified water | q.s. |

Other compounds having a structure according to Formula (I) are used with substantially similar results.

Example 11

An inhalation aerosol composition, according to the present invention, is made comprising:

| Component | Composition (% w/v) |
| --- | --- |
| Compound of Example 3 | 5.0 |
| Ascorbic acid | 0.1 |
| Menthol | 0.1 |
| Sodium Saccharin | 0.2 |
| Propellant (F12, F114) | q.s. |

Other compounds having a structure according to Formula (I) are used with substantially similar results.

Example 12

A topical opthalmic composition, according to the present invention, is made comprising:

| Component | Composition (% w/v) |
| --- | --- |
| Compound of Example 1 | 0.10 |
| Benzalkonium chloride | 0.01 |
| EDTA | 0.05 |
| Hydroxyethylcellulose | 0.5 |
| Acetic acid | 0.20 |
| Sodium metabisulfite | 0.10 |
| Sodium chloride (0.9%) | q.s. |

Other compounds having a structure according to Formula (I) are used with substantially similar results.

Example 13

An antimicrobial composition for parenteral administration, according to this invention, is made comprising:

| Component | Amount |
| --- | --- |
| Compound of Example 2 | 30 mg/ml excipient |
| Excipient: | |
| 50 mm phosphate buffer pH 5 buffer with lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 ml of the suspension is systemically administered, via intramuscular injection, to a human subject suffering from a lower respiratory tract infection, with *Streptococcus pneumoniae* present. This dosage is repeated twice daily, for approximately 14 days. After 4 days, symptoms of the disease subside, indicating that the pathogen has been substantially eradicated. Other compounds having a structure according to Formula (I) are used with substantially similar results.

Example 14

An enteric coated antimicrobial composition for oral administration, according to this invention, is made comprising the following core tablet:

| Component | Amount (mg) |
|---|---|
| Compound of Example 6 | 350.0 |
| Maltodextrine | 30.0 |
| Magnesium Stearate | 5.0 |
| Microcrystalline Cellulose | 100.0 |
| Colloidal Silicon Dioxide | 2.5 |
| Povidone | 12.5 |

The components are admixed into a bulk mixture. Compressed tablets are formed, using tabletting methods known in the art. The tablet is then coated with a suspension of methacrylic acid/methacrylic acid ester polymer in isopropanol/acetone. A human subject, having a urinary tract infection with *Escherichia coli* present, is orally administered two of the tablets, every 8 hours, for 4 days. Symptoms of the disease then subside, indicating substantial eradication of the pathogen. Other compounds having a structure according to Formula (I) are used with substantially similar results.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to Formula (I)

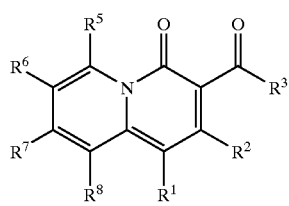

wherein:
(A)
(1) $R^1$ is selected from $C_3$ to about $C_6$ cycloalkyl, $C_4$ to about $C_6$ heterocycloalkyl, $C_1$ to about $C_6$ alkyl, $C_2$ to about $C_6$ alkene, a 6-membered aryl, and a 6-numbered heteroaryl;
(2) $R^2$ is hydrogen;
(3) $R^3$ is selected from hydrogen and hydroxy;
(4) $R^5$ is selected from hydrogen, hydroxy, amino, halo, $C_1$ to about $C_6$ alkyl, $C_2$ to about $C_6$ alkene, and $C_1$ to about $C_6$ alkoxy;

(5) $R^6$ is selected from hydrogen, hydroxy, aminocarbonyl, cyano, $C_1$ to about $C_4$ alkyl, an $C_2$ to about $C_4$ alkene; all such alkyl and alkene moieties being unsubstituted or substituted with from 1 to about 3 fluoro, or in the case of methyl or ethyl, optionally substituted with one hydroxy or one amino moiety;
(6) $R^7$ is selected from

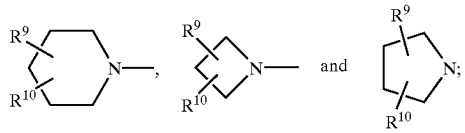

wherein
(a) $R^9$ is (i) amino which is attached to a ring carbon of $R^7$ which is not adjacent to the ring nitrogen of $R^7$, the amino being unsubstituted or substituted with one or two $C_1$ to about $C_3$ alkyl; or (ii) aminoalkyl which is attached to any ring carbon of $R^7$ and is $C_1$ to about $C_3$ alkyl substituted with one amino, the amino being unsubstituted or substituted with one or two $C_1$ to about $C_3$ alkyl; and
(b) $R^{10}$ represents the moieties on $R^7$ other than $R^9$ and each $R^{10}$ is independently selected from hydrogen, $C_1$ to about $C_4$ alkyl, $C_2$ to about $C_6$ alkene, and a $C_3$ to about $C_6$ fused or spirocycle alkyl ring; all alkyl, alkene and cycle $R^{10}$ moieties being unsubstituted or substituted with one hydroxy or with from 1 to about 3 fluoro moieties; and
(7) $R^8$ is selected from halo, $C_1$ to about $C_6$ alkoxy, $C_1$ to about $C_6$ alkylthio, $C_1$ to about $C_6$ alkyl and $C_2$ to about $C_6$ alkene;

or an optical isomer, diastereomer or enantiomer thereof; or a phamaceutically-acceptable salt, hydrate, or biohydrolyzable ester, amide or imide thereof.

2. A compound of claim 1 wherein $R^1$ is selected from $C_3$ to about $C_6$ cycloalkyl, a 6-membered aryl, $C_1$ to about $C_2$ alkyl, and $C_2$ to about $C_3$ alkene.

3. A compound of claim 2 wherein $R^1$ is selected from cyclopropyl, ethyl, 4-hydroxyphenyl, and 2,4-difluorophenyl.

4. A compound of claim 1 wherein $R^3$ is hydroxy.

5. A compound of claim 1 wherein $R^5$ is selected from hydrogen, hydroxy, chloro, bromo, amino, methyl, monofluoromethyl, difluoromethyl, and trifluoromethyl.

6. A compound of claim 1 wherein $R^6$ is selected from hydrogen, hydroxy, methyl, monofluoromethyl, difluoromethyl, and trifluoromethyl.

7. A compound of claim 6 wherein $R^6$ is hydrogen.

8. A compound of claim 1 wherein $R^8$ is selected from chloro, methyl, methoxy, methylthio, monofluoromethyl, difluoromethyl, trifluoromethyl, monofluoromethoxy, difluoromethoxy, and trifluoromethoxy.

9. A compound of claim 1 wherein $R^7$ is selected from:

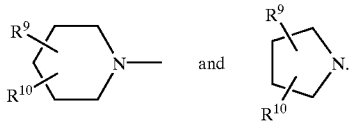

10. A compound of claim 1 wherein $R^9$ is amino, unsubstituted or substituted with one or two alkyl moieties independently selected from methyl and ethyl.

11. A compound of claim 10 wherein $R^9$ is —$NH_2$.

12. A compound of claim 1 wherein $R^9$ is aminoalkyl, wherein the alkyl is unsubstituted or substituted with one or more $C_1$ to about $C_6$ alkyl groups and the amino is unsubstituted or substituted with one or two alkyl moieties independently selected from methyl and ethyl.

13. A compound of claim 12 wherein $R^9$ is selected from aminomethyl, methylaminomethyl, 1-aminoethyl, 1-methylaminoethyl, 1-amino-1-methylethyl, and 1-methylamino-1-methylethyl.

14. A compound of claim 1 wherein each $R^{10}$ is independently selected from hydrogen and $C_1$ to about $C_6$ alkyl.

15. A compound of claim 14 wherein not more than one $R^{10}$ is other than hydrogen.

16. A pharmaceutical composition comprising:
(a) a safe and effective amount of a compound of claim 1; and
(b) a pharmaceutically-acceptable excipient.

17. A method for treating microbial infection comprising administering to a host in need of such a treatment a safe and antimicrobially effective amount of a compound of claim 1.

* * * * *

UNITED STATES PATENT AND TRADEMARK OFFICE
CERTIFICATE OF CORRECTION

PATENT NO. : 6,509,349 B1
DATED : January 21, 2003
INVENTOR(S) : Benoit Ledoussal et al.

It is certified that error appears in the above-identified patent and that said Letters Patent is hereby corrected as shown below:

Column 26,
Line 62, delete "pharrnaceutically" and insert therefor -- pharmaceutically --.

Column 29,
Line 6, Precursor Example A, arrow is ponting to the right; reverse direction.

Column 31,
Line 62, delete "mnl" and insert therefor -- ml --.

Column 33,
Line 20, insert therefor -- (Precursor C) --.

Column 40,
Line 35, insert missing section of Claim 1, after number (7) therefor
-- (B)   $R^8$ and $R^1$ can join to form a 6-membered heterocyclic ring, where $R^2$, $R^3$, $R^5$, $R^6$ and $R^7$ are as described in (A); --.
Line 37, delete "phanmaceutically" and insert therefor -- pharmaceutically --.

Signed and Sealed this

Third Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,509,349 B1
DATED : January 21, 2003
INVENTOR(S) : Benoit Ledoussal et al.

It is certified that error appears in the above-identified patent and that said Letters Patent is hereby corrected as shown below:

Column 12,
Line 34, delete "invention".

Column 22,
Line 48, delete "$R^5$" and insert therefor -- $R^8$ --.

Signed and Sealed this

Third Day of August, 2004

JON W. DUDAS
*Acting Director of the United States Patent and Trademark Office*